United States Patent

Schroeder et al.

[11] Patent Number: 5,324,477
[45] Date of Patent: Jun. 28, 1994

[54] PROCESS FOR DISINFECTING HARD SURFACES WITH CHLORINE DIOXIDE

[75] Inventors: Karl-Heinz Schroeder, Duesseldorf, Fed. Rep. of Germany; Wolfgang Falter, Lichtenbosch, Belgium; Walter Grosse-Boewing, Dormagen, Fed. Rep. of Germany

[73] Assignee: Henkel Komnmanditgesellschaft auf Aktien, Duesseldorf, Fed. Rep. of Germany

[21] Appl. No.: 836,314
[22] PCT Filed: Aug. 21, 1990
[86] PCT No.: PCT/EP90/01377
§ 371 Date: Feb. 28, 1992
§ 102(e) Date: Feb. 28, 1992
[87] PCT Pub. No.: WO91/03265
PCT Pub. Date: Mar. 21, 1991

[30] Foreign Application Priority Data

Aug. 30, 1989 [DE] Fed. Rep. of Germany ....... 3928747

[51] Int. Cl.$^5$ .......................... C23F 11/00; A01N 37/00
[52] U.S. Cl. ........................................... 422/37; 422/7; 134/3
[58] Field of Search .......................... 422/37, 7, 12, 29; 134/3

[56] References Cited

U.S. PATENT DOCUMENTS

| | | | |
|---|---|---|---|
| 4,504,442 | 3/1985 | Rosenblatt et al. | 422/37 |
| 4,681,739 | 7/1987 | Rosenblatt et al. | 422/37 |
| 4,731,193 | 3/1988 | Mason et al. | 422/37 X |
| 4,747,975 | 5/1988 | Ritter | 134/3 X |

FOREIGN PATENT DOCUMENTS

| | | |
|---|---|---|
| 0153841 | 9/1985 | European Pat. Off. . |
| 3218649 | 11/1983 | Fed. Rep. of Germany . |
| 76082080 | 7/1976 | Japan . |
| 84187668 | 4/1983 | Japan . |
| 85054923 | 3/1985 | Japan . |
| 60-259671 | 12/1985 | Japan . |
| 85259571 | 12/1985 | Japan . |
| 86145300 | 7/1986 | Japan . |
| 88008203 | 1/1988 | Japan . |
| 83161903 | 9/1988 | Japan . |
| 1171425 | 7/1989 | Japan . |
| 8301940 | 6/1983 | World Int. Prop. O. . |
| 8401507 | 4/1984 | World Int. Prop. O. . |
| 8504107 | 9/1985 | World Int. Prop. O. . |

OTHER PUBLICATIONS

Webster's New Collegiate Dictionary, p. 617.

Primary Examiner—Robert J. Warden
Assistant Examiner—E. Leigh Dawson
Attorney, Agent, or Firm—Ernest G. Szoke; Wayne C. Jaeschke; Henry E. Millson, Jr.

[57] ABSTRACT

Method for disinfecting hard surfaces by treating the hard surfaces with an aqueous composition containing from 2 to 40% by weight of a sodium chlorite and from 1 to 60% by weight of at least one nitrogen-free acidic scale inhibiting agent. The composition generates chlorine dioxide in situ and also acts as a water hardness stabilizer and corrosion inhibitor.

15 Claims, No Drawings

PROCESS FOR DISINFECTING HARD SURFACES WITH CHLORINE DIOXIDE

This invention relates to a process for disinfecting hard surfaces under water-hardness-stabilized and non-corrosive conditions with chlorine dioxide produced in solution by mixing of a solution of sodium chlorite and another acidic component in a generator.

Chlorine dioxide is a disinfectant which has advantages over chlorine, alkali metal or alkaline earth metal hypochlorites, organic chlorine donors and other disinfectants based on active chlorine, above all in the disinfection of bottles, containers, equipment and pipes. Chlorine dioxide forms hardly any trihalomethanes (haloforms) and hardly any relatively high molecular weight organohalogen compounds. In contrast to chlorine, chlorine dioxide does not react with phenols to form chlorophenols which are responsible for the medicated taste in the washing of mineral water and table water bottles. Nor does chlorine dioxide react with amino or ammonium compounds to form chloramines or ammonium chlorides. The effectiveness (redox potential) of chlorine dioxide, which in addition is largely unaffected by pH, is two to three times stronger than that of chlorine. However, this becomes even clearer by comparison with peracids which are also used for disinfection. In addition to greater effectiveness, this results in the use of lower concentrations and, hence, in less wastewater pollution.

In addition to good bactericidal activity, chlorine dioxide also shows good sporicidal, virucidal and algicidal properties. Chlorine dioxide is a powerful disinfectant which affords long-lasting bactericidal and bacteriostatic protection. In addition to its use as a disinfectant, chlorine dioxide—by virtue of its high oxidation potential—is also effective in eliminating unpleasant odors, tastes and colors in the treatment of water. In addition, it reacts with organic bound iron and manganese (for example in huminic and fulvic acids) and degrades carcinogenic substances, such as polycyclic aromatic compounds. In the pretreatment of raw waters or surface waters, chlorine dioxide improves flocculation so that it is preferably used for the disinfection of drinking water. Chlorine dioxide is also used for its disinfecting effect in the food and beverage industry, for example in the disinfection of filling machines, bottle washing machines and pasteurizers, as feed and return water and as washing and rinsing water. In this particular field of application, problems are caused above all by precipitations, particularly of water hardness, which begin in particular at pH values of 10.5 to 11.5 and/or at temperatures above 54° C. However, unwanted precipitation of water ingredients, especially water hardness, also occur at relatively low and relatively high pH values and/or temperatures.

The process used at the present time for the production of chlorine dioxide is based on the chlorine/chlorite process (1) or on the hydrochloric acid/chlorite process (2). The chlorine/chlorite process is preferably used in municipal water treatment (large users) while the hydrochloric acid/chlorite process is used in industry (small and medium users).

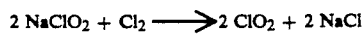

(1)

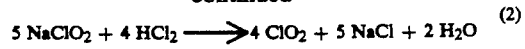

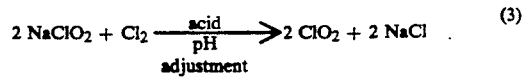

In the chlorine/chlorite process (1), a certain excess of chlorine has to be used to obtain a complete reaction in accordance with the reaction equation, with the result that excess chlorine is always present in use. If the chlorine is used in a stoichiometric quantity, the reaction is always incomplete.

In the hydrochloric acid/chlorite process (2), the chlorine dioxide solutions obtained show less contamination, although the maximum theoretical yield, based on chlorite, is limited to 80% by the stoichiometry of the reaction equation. In addition to hydrochloric acid, other acids may also be used.

The three-component process (3) is based on the chlorine/chlorite process (1) and, through the use of additional acid, guarantees a substantially complete chlorite conversion due to the reduction in the pH value.

The disadvantage of the processes industrially used at the present time lies in their corrosive effect because hydrochloric acid is used in a large excess in the hydrochloric acid/chlorite process (2). Hydrochloric acid and chlorine are known to contribute particularly towards pitting, particularly in stainless steels. In addition, the occasionally high concentrations of sodium chloride released in these processes are another disadvantage. Accordingly, the disinfection processes are confined to certain applications.

The object of WO 85/04107 is to replace the aggressive hydrochloric acid by α-hydroxycarboxylic acids. According to JP 86/145 300, acetic acid, sulfuric acid, citric acid or malonic acid is used for the production of chlorine dioxide. The chlorine dioxide thus produced is used for the disinfection of fishing nets. JP 76/082 080 also uses citric acid for the production of bleaching baths. According to JP 60/259 671, a mixture of sodium chlorite or chlorous acid and organic phosphonic acids is used for bleaching fibers. According to WO 84/01507, chlorine dioxide generated from various acids may be used for sterilizing medical instruments. JP 84/187 668 describes the release of chlorine dioxide using tetrachloroethylene in oxygen while U.S. Pat. No. 4,542,008 and U.S. Pat. No. 4,432,856 describe the electrolytic composition of sodium chlorite to chlorine dioxide.

In addition to the production of chlorine dioxide from sodium chlorite and acid, there are known processes for the production of chlorine dioxide from chlorate and chloric acid using various reducing agents, such as hydrogen peroxide (JP 88/008 203), chloride and acid (EP 153 841), chloride and heat (U.S. Pat. No. 4,678,653), sulfur dioxide and acid (WO 83/01940), hydrochloric acid (DE 32 18 649), alcohols and acid (U.S. Pat. No. 4,627,969), manganese(II) salts (JP 85/054 923), hypochlorite and acid (JP 83/161 903) and palladium-(II) salts (U.S. Pat. No. 4,421,730).

Nevertheless, there are no known processes which enable the high corrosiveness of chlorine dioxide in its various applications to be controlled. Apart from these unsolved corrosion problems, the fact that it promotes hardness precipitation when used in hard water coupled with the high salt levels in the wastewater have also prevented the wide-scale use of chlorine dioxide. In addition, these disadvantages preclude the use of chlorine dioxide in other fields of application.

Accordingly, the problem addressed by the present invention was to provide a process for the disinfection of hard surfaces using chlorine dioxide which would reduce corrosion and prevent precipitations, particularly of water hardness. In addition, the level of sodium chloride in the wastewaters would be reduced.

According to the invention, this problem has been solved by a process for disinfecting hard surfaces under water-hardness-stabilized and non-corrosive conditions with chlorine dioxide produced in solution by mixing of a solution of sodium chlorite and an acidic component in a generator, characterized in that the concentration of the sodium chlorite solution is between 2 and 40% by weight and a sequestering agent or a complexing agent or mixtures of sequestering agents and complexing agents is/are used as the acidic component and as the water hardness stabilizer and corrosion inhibitor, the sequestering agent and/or the complexing agent being used in a concentration of 1 to 60% by weight and having a pH value of <7 in the form of a 1% aqueous solution and the concentration of chlorine dioxide being between 0.1 and 500 ppm.

Complexing and sequestering agents suitable for the stated purpose are also characterized in that, in one or more tests A, B, C (warm water zone simulator, scaling behavior in the alternate immersion test and calcium binding power), they show better scale inhibition than the corresponding water value.

In a preferred embodiment, the sequestering agent or complexing agent has a pH value of <3 in the form of a 1% aqueous solution and the chlorine dioxide concentration is between 0.1 and 100 ppm. Chlorine dioxide concentrations of 0.1 to 20 ppm and, more particularly, 0.5 to 5 ppm are particularly preferred for the process according to the invention.

The concentration of the sequestering agent and/or the complexing agent is preferably in the range from 15 to 25% by weight.

Suitable sequestering agents or complexing agents are, for example, phosphonic acids, polyphosphoric acid, acrylic acid, methacrylic acid, polyacrylic acid and polymethacrylic acid. However, other sequestering or complexing agents which pass one or more of tests A, B and C may also be used. Particularly preferred phosphonic acids, which have a pH value of <7 and preferably <3 in the form of a 1% aqueous solution and which pass one or more of tests A, B and C, are 1-hydroxyethane-1,1-diphosphonic acid and 2-phosphonobutane-1,2,4-tricarboxylic acid.

Examples of other phosphonic acids which may be used in accordance with the invention are 2,2-diphosphonobutane-3,4-dicarboxylic acid, 1-phosphonopropane-1,2,3-tricarboxylic acid, 1,1-diphosphonopropane-2,3-dicarboxylic acid and methylene diphosphonic acid.

By contrast, N-containing sequestering and complexing agents do not always release the chlorine dioxide in the desired manner for the process according to the invention.

Mixtures of the above-mentioned sequestering and/or complexing agents with carboxylic acids and/or hydroxycarboxylic acids containing one or more carboxyl groups may also be used as acidic components in the process according to the invention for disinfecting hard surfaces. Suitable carboxylic acids and/or hydroxycarboxylic acids are, for example, citric acid, tartaric acid, malic acid, oxalic acid, maleic acid, malonic acid, succinic acid, adipic acid, glycolic acid, lactic acid or gluconic acid. Accordingly, 2-phosphonobutane-1,2,4-tricarboxylic acid and/or 1-hydroxyethane-1,1-diphosphonic acid are preferably used together with citric acid in the process according to the invention. The citric acid may even be replaced by, in particular, oxalic acid, lactic acid or gluconic acid. The quantity of carboxylic acid or hydroxycarboxylic acid added is arbitrary and may be varied within wide limits. In general, the mixing ratio (based on molar ratios) of sequestering and/or complexing agent to carboxylic acid or hydroxycarboxylic acid is in the range from 10:1 to 1:10, preferably in the range from 2:1 to 1:2 and, more preferably, is 1:1. Additions such as these in the process according to the invention synergistically increase the yield of chlorine dioxide and provide for better scale inhibition.

In another embodiment of the present invention, Lewis acids may be used as acidic components in addition to the sequestering and/or complexing agents mentioned or in addition to the above-described combination of sequestering agents with carboxylic acids or hydroxycarboxylic acids. Preferred Lewis acids are iron and/or aluminium salts, more particularly the corresponding sulfates, nitrates or chlorides. The quantity in which the Lewis acids are added is again arbitrary and may be varied within wide limits. Mixing ratios (based on molar ratios) of sequestering agents or sequestering agents and carboxylic acids or hydroxycarboxylic acids to Lewis acids of 1:2 to to 3:1 are preferred.

The reaction path is characterized by the following general formula scheme:

$$5\ NaClO_2 + 4/n\ (R-XH_n)_m \longrightarrow 4\ ClO_2 +$$

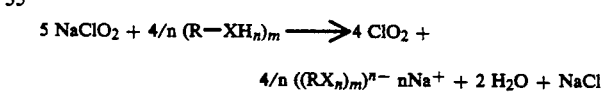

$$4/n\ ((RX_n)_m)^{n-}\ nNa^+ + 2\ H_2O + NaCl$$

The sequestering agents are characterized by the fact that they are used in far less than equimolar quantities, based on the cation of which the crystal formation is to be prevented. This means, for example, that less than 100 ppm and preferably less than 50 ppm active substance are required for 1° d—German hardness—(in 1% NaOH). By contrast, complexing agents are used in a concentration equal to or higher than the concentration required for stoichiometric water hardness stabilization.

The chlorine dioxide/corrosion inhibitor/hardness stabilizer solutions according to the invention, which may be generated from only two components by this single-stage process, may be used for other applications, including in particular the spray and foam external cleaning of plant, the disinfection of drinking water circuits, membrane units, tanks, containers and filling machines. They may also be used as a cleaning and, above all, disinfecting additive for chain lubricants.

Since the solutions produced by the process according to the invention combine the effects of a disinfectant, a water hardness stabilizer and a corrosion inhibitor, they may be used in particular in bottle washing machines, tunnel pasteurizers, re-coolers, filter units, for disinfecting cooling water and for cleaning casks and containers. Hitherto, additional components had to be used as hardness stabilizers and corrosion inhibitors in addition to chlorine dioxide and had to be added to the known solutions. The process according to the invention eliminates the need to use an additional hardness stabilizer and corrosion inhibitor. The addition of a detergent, a detergency booster, surfactants and other auxiliaries and additives typical of the particular application generally does not affect the performance or application of the process according to the invention.

The advantages are illustrated with reference by way of example to the phosphonic acids preferably used, for example 2-phosphonobutane-1,2,4-tricarboxylic acid. The alkali metal phosphonates accumulating as secondary products and free phosphonic acid still present in an additional excess stabilize water hardness, i.e. calcium and magnesium ions. This is even the case when the sequestering and complexing agents are present as alkali metal salts in an alkaline disinfecting solution. There is no need to use additional complexing and sequestering agents. Because no aggressive inorganic acids are used, the corrosive effect on brass, copper, stainless steel and aluminium is reduced. The saving of two further components makes the process according to the invention cost-effective and safer to carry out in practice.

In addition, the effectiveness of the process for disinfection, hardness stabilization and corrosion inhibition can be freely controlled through the use of an excess of acidic component, i.e. for particularly hard water, it is possible to add correspondingly more than only the equimolar quantity of sequestering or complexing agent without at the same time reducing the disinfecting effect or the level of corrosion inhibition.

Tests A, B and C for determining the complexing and sequestering properties are described by way of example in the following for special compounds.

Test A

The scale-inhibiting behavior of the disinfecting solutions according to the invention was tested in a warm water zone (50±0.5° C.) into which a cleaned and weighed chrome/nickel steel plate (V 4A) of known surface had been introduced. The throughflow of factory water having a hardness of 16° d was 25 l/h and the duration of the test 6 h at various pH values of 9, 10, 11 and 12. The test plate was then removed and weighed. For a pH value of 10 and an addition of sequestering agent of 30 g/m$^3$/h, scale formation amounted to less than 0.2 g/m$^3$/h. For a pH value of 11 and an addition of sequestering agent of 50 g/m$^3$/h, scale formation amounted to less than 0.5 g/m$^3$/h.

A mixture of 2-phosphonobutane-1,2,4-tricarboxylic acid and citric acid in a molar ratio of 1:1 was used as the sequestering agent.

Test B

Scaling behavior can also be determined by an alternate immersion test in which a metal test plate or glass is immersed for 2 minutes in a bath containing the disinfecting solution and for 2 minutes in a rinsing bath (water) and is subsequently dried. In one example, scaling of 0 g/cm$^2$ on the metal plate and 0.3 g/m$^2$ on the glass was observed for 1-hydroxyethane-1,1-diphosphonic acid as the acidic component in 1% NaOH, corresponding to maximum scaling of 1 g/m$^2$, but preferably less than 0.5 g/m$^2$ per 1° d.

Test C

Determination of the calcium and magnesium binding power (CaBp and MgBp) was carried out as follows:

After determination of the ignition residue values, the approximate quantity of active substance (As) weighed in was determined as a function thereof. The quantity of active substance should amount to approx. 200 mg. The quantities weighed in on an analytical balance are then introduced into a 300 ml Erlenmeyer flask and, after the addition of 200 ml water of 30° d or 6° d, are stirred for 10 minutes. The samples are then filtered under suction through a nutsche or frit. 100 ml of the filtrate are pipetted off and one indicator buffer tablet (ammonium chloride, Merck, Article No. 8430) is added. After the tablet has dissolved, 5 ml concentrated ammonia solution are added. The solution is then titrated with N/28 Komplexon ® solution (change in color from red to green) and the consumption (C) is determined. A blank test (Bt), in which no active substance is weighed in, is carried out under the same conditions.

1° d = 10 mg CaO/l or MgO/l . F (0.719)

Calculation
for water of 6° d (German hardness):

$$CaBp = \frac{(Bt - C) \cdot 2}{As \text{ (in g)} \cdot 5} \; ; \; MgBp = \frac{(Bt - C) \cdot 2 \cdot 0.719}{As \text{ (in g)} \cdot 5}$$

for water of 30° d (German hardness):

$$CaBp = \frac{(Bt - C) \cdot 2}{As \text{ (in g)}} \; ; \; MgBp = \frac{(Bt - C) \cdot 2 \cdot 0.719}{As \text{ (in g)}}$$

The result is expressed in mg CaO/g As or mg MgO/g As.

Test D

Determination of the chlorine dioxide concentration:

The chlorine dioxide solution was prepared in a standard chlorine dioxide generator by mixing a 2 to 40% sodium chlorite solution with a 1 to 60% solution of the acidic component at room temperature. In a characteristic example, the concentration of the sodium chlorite solution was 7.5% and the concentration of the acidic component between 15 and 25%. A mixture of 2-phosphonobutane-1,2,4-tricarboxylic acid and citric acid in a molar ratio of 1:1 was used as the acidic component. The reaction temperature can be varied from 0° C. to 60° C. to change the equilibrium adjustment of the chlorine dioxide. To obtain homogeneous and continuous chlorine dioxide concentrations, an average holding time of 30 seconds to 20 minutes is necessary before use. The effectiveness of the chlorine dioxide and of sequestering is developed immediately after passing through the reaction zone.

A BelloZon CD 035 generator manufactured by the ProMinent company of D-6900 Heidelberg was used as a standard generator. However, simple dispensers or mechanical apparatus in which both components are simply mixed together and hence reacted may be used for smaller applications (for example for instrument disinfection in hospitals). Plants in which the chemicals are added in concentrated form and the formation of explosive chlorine dioxide concentrations in the in-use solution is prevented by means of a dilution pump are suitable for applications involving larger surface areas.

The chlorine dioxide concentration was determined photometrically using N,N-diethyl-1,4-phenylenediamine as redox initiator or on-line by amperometry. Concentrations of 0.1 to 20 ppm and preferably 0.5 to 5 ppm were determined. Concentrations of 2 ppm are generally sufficient for standard applications. The chlorine dioxide concentration can be controlled through the ratio of the concentration of the acidic component to sodium chloride.

The yields of chlorine dioxide obtained were up to 97% of the theoretical.

EXAMPLES

The above-mentioned Bellozon CD 035 generator was used as the reactor for the following Examples. A 7.5% by weight aqueous sodium chlorite solution was introduced into the reactor and thoroughly mixed with the particular "acidic component" or acid (see the individual Examples).

The reaction proceeds in accordance with the following general equation: 5 mol $NaClO_2$ + 4 mol acid → 4 mol $ClO_2$ + 5 mol salt + 2 mol $H_2O$. According to this equation, an addition of 4 mol acid or acidic component to 5 mol sodium chlorite is sufficient for a stoichiometric conversion. In the following Examples, however, the particular acidic component was used in an excess of approx. 10 mol, based on the above molar ratio.

To determine the yield of chlorine dioxide using various acidic components, the chlorine dioxide content of the solution (in ppm) was compared with the maximum theoretical concentration obtainable in the HCl/chlorite process. In this case, the conversion amounts to 8.42 ppm chlorine dioxide, corresponding to a 100% conversion, based on the following Examples.

1. The following constituents were used:
5 mol $NaClO_2$ = 452.2 g
14.2 mol "acidic component" consisting of:
  6.12 mol citric acid = 1,175.6 g
  2.89 mol 2-phosphonobutane-1,2,4-tricarboxylic acid (Bayhibit ®AM, Bayer AG) = 779.3 g
  2.29 mol 1-hydroxyethane-1,1-diphosphonic acid (Turpinal ®SL, a product of Henkel KGaA) = 470.9 g
  2.90 mol polyacrylic acid (Sokalan ®DCS, a product of BASF AG) = 391.8 g.
Yield: 3.88 mol $ClO_2$ (= 261.7 g), corresponding to 97% of the theoretical.

The following Examples were carried out in the same way:

2) Acid: 1-hydroxyethane-1,1-diphosphonic acid, yield: 6.2 ppm $ClO_2$ (= 74% of the theoretical).

3) Acid: 2-phosphonobutane-1,2,4-tricarboxylic acid yield: 6.75 ppm $ClO_2$ (= 80% of the theoretical).

4) Acid: polyacrylic acid (Sokalan ® PA, a product of BASF AG) yield: >6 ppm $ClO_2$ (>71% of the theoretical).

5) Acid: polyphosphoric acid yield: 6.3 ppm $ClO_2$ (= 75% of the theoretical).

6) Acid: mixture of 2-phosphonobutane-1,2,4-tricarboxylic acid and citric acid in a molar ratio of 1:1 yield: 8.16 ppm $ClO_2$ (= 97% of the theoretical).

We claim:

1. A method for disinfecting a hard surface comprising contacting said hard surface with an aqueous composition comprising
   (a) from 2 to 40% by weight of sodium chlorite,
   (b) from 1 to 60% by weight of at least one nitrogen-free acidic scale inhibiting agent selected from the group consisting of a phosphonic acid, polyphosphoric acid, acrylic acid, methacrylic acid, polyacrylic acid, and polymethacrylic acid, wherein a 1% aqueous solution of the at least one scale inhibiting agent has a pH of less than 7, and wherein this component acts as an acidic component to produce a chlorine dioxide concentration in the aqueous composition of from 0.1 to 500 ppm and also functions as a water hardness stabilizer and metal corrosion inhibitor, and
   (c) at least one carboxylic acid selected from the group consisting of tartaric acid, malic acid, oxalic acid, maleic acid, malonic acid, succinic acid, adipic acid, glycolic acid, lactic acid, gluconic acid, and citric acid, wherein the molar ratio of component b) to component c) is from 10:1 to 1:10.

2. The method of claim 1 wherein in the aqueous composition a 1% aqueous solution of component b) has a pH of less than 3, and the chlorine dioxide concentration in the aqueous composition is from 0.1 to 100 ppm.

3. The method of claim 2 wherein component b) is at least one of 1-hydroxyethane-1,1-diphosphonic acid and 2-phosphonobutane-1,2,4-tricarboxylic acid.

4. The method of claim 1 wherein in the aqueous composition component b) is present in the composition in from 15 to 25% by weight.

5. The method of claim 1 wherein the aqueous composition contains more than the theoretical quantity of component b) based on component a).

6. The method of claim 1 wherein the chlorine dioxide concentration in the aqueous composition is between 0.1 and 20 ppm.

7. The method of claim 6 wherein the chlorine dioxide concentration is between 0.5 and 5 ppm.

8. The method of claim 1 wherein component c) of the aqueous composition is lactic acid or citric acid.

9. The method of claim 1 wherein the aqueous composition also contains a Lewis acid.

10. The method of claim 9 wherein the Lewis acid is a sulfate, nitrate, or chloride of iron or aluminum.

11. The method of claim 9 wherein the molar ratio of component b) plus c) to the Lewis acid is from 1:2 to 3:1.

12. The method of claim 1 wherein the ratio of component b) to component c) is from 2:1 to 1:2.

13. The method of claim 1 wherein in the aqueous composition a 1% solution of component b) has a pH of less than 3; the chlorine dioxide concentration is from 0.1 to 20 ppm; component b) is present in the composition in from 15 to 25% by weight; and the ratio of component b) to component c) is from 2:1 to 1:2.

14. The method of claim 13 wherein component b) is at least one of 1-hydroxyethane-1,1-diphosphonic acid and 2-phosphonobutane-1,2,4-tricarboxylic acid and component c) is lactic acid or citric acid.

15. The method of claim 13 wherein a Lewis acid is also present in the aqueous composition in a molar ratio of component b) plus component c) to the Lewis acid of from 1:2 to 3:1.

* * * * *